United States Patent
Matloub

(10) Patent No.: US 10,016,584 B1
(45) Date of Patent: Jul. 10, 2018

(54) MULTILAYERED DEVICE FOR CONTROLLED TOPICAL DELIVERY OF THERAPEUTIC AGENTS TO THE SKIN

(71) Applicant: Haitham Matloub, Waukesha, WI (US)

(72) Inventor: Haitham Matloub, Waukesha, WI (US)

(73) Assignee: New Medical Technology, Inc., Northbrook, IL (US)

( * ) Notice: Subject to any disclaimer, the term of this patent is extended or adjusted under 35 U.S.C. 154(b) by 0 days.

(21) Appl. No.: 14/970,173

(22) Filed: Dec. 15, 2015

Related U.S. Application Data

(63) Continuation of application No. 11/965,904, filed on Dec. 28, 2007, now abandoned, which is a continuation-in-part of application No. 10/751,189, filed on Jan. 2, 2004, now Pat. No. 7,316,817.

(51) Int. Cl.
*A61M 35/00* (2006.01)
*A61L 26/00* (2006.01)

(52) U.S. Cl.
CPC ......... *A61M 35/00* (2013.01); *A61L 26/0066* (2013.01); *A61L 26/0085* (2013.01); *A61L 26/0095* (2013.01); *A61L 2430/34* (2013.01)

(58) Field of Classification Search
None
See application file for complete search history.

(56) References Cited

U.S. PATENT DOCUMENTS

| | | | | |
|---|---|---|---|---|
| 3,948,254 A | * | 4/1976 | Zaffaroni | A61M 31/002 128/833 |
| 6,231,879 B1 | * | 5/2001 | Li | A61K 9/0024 424/422 |
| 2003/0077311 A1 | * | 4/2003 | Vyakarnam | A61F 2/28 424/426 |
| 2008/0131493 A1 | * | 6/2008 | Matloub | A61K 8/0208 424/449 |

FOREIGN PATENT DOCUMENTS

EP 251631 A * 1/1998

* cited by examiner

*Primary Examiner* — Isis A Ghali
(74) *Attorney, Agent, or Firm* — Dennis IP Law Group, LLC; W. Dennis Drehkoff

(57) ABSTRACT

A multilayered composite sheet for delivering one or more therapeutic agents to the skin is disclosed. The composite sheet comprises a flexible porous polymer with open cells of a sufficient size for holding a therapeutic agent, an encapsulating agent for encapsulating the flexible porous polymer and therapeutic agent, and an enrobing agent for enrobing the encapsulated flexible porous polymer and therapeutic agent. Additional layers of the flexible porous polymer, therapeutic agent and other materials are added to the first layer which is in contact with the skin. The first layer has particular particle sizes for the flexible porous polymer, open cell size, and therapeutic agent allowing for relatively quick delivery of the therapeutic agent to the skin. Each successive layer placed on top of the first layer has incrementally larger particle sizes of the flexible porous polymer and therapeutic agent providing successively longer delivery times than the first layer.

20 Claims, 3 Drawing Sheets

MULTILAYERED DEVICE FOR CONTROLLED TOPICAL DELIVERY OF THERAPEUTIC AGENTS TO THE SKIN

RELATED APPLICATIONS

This application claims the benefit of and is a continuation of U.S. patent application Ser. No. 11/965,904 filed on Dec. 28, 2007, abandoned, which is a continuation-in-part of U.S. patent application Ser. No. 10/751,189, filed on Jan. 2, 2004, now U.S. Pat. No. 7,316,817, which are fully incorporated herein by reference.

FIELD OF THE INVENTION

This invention relates to an improved device for the controlled delivery of therapeutic agents to the skin. It may also be used for the treatment of various dermatological conditions, diseases, wounds, and burns.

BACKGROUND

Currently, there are various delivery systems for the topical application of pharmaceutical compounds, for example, lotions, creams, gels, ointments, transdermal patches, and sprays. Typically, the selection of a delivery system depends upon the desired pharmacokinetic profile of the specific therapeutic agent, for example, whether immediate, short-term, or sustained release is required for the administration of the therapeutic agent. Occlusion problems are common with many of the systems, and they may also cause skin irritation. Many pharmaceutical compounds, for example, hormonal drugs, are conveniently delivered using a transdermal patch. Typically, the patch is comprised of an occlusive vacuum membrane, which often results in a local skin irritation. In addition, with transdermal patches, the penetration of the drug into the skin is often poor. With reference to conventional topical spray formulations, the therapeutic agent tends to remain at the application site for only a short period of time and can be easily rubbed off or made unavailable for penetration into the skin.

The preparation of controlled drug delivery systems for topical application is often more of an art than a science. Many factors directly affect the release rate of a therapeutic agent, and oftentimes, the correct formulation for efficient delivery of a therapeutic agent is found by trial and error.

Controlled release of topic drug delivery occurs when a polymer is measurably combined with an active agent or therapeutically active agent in such a way that the active agent is released from the polymer at a controlled rate. The release of the active agent may be constant over a period of time, may be cyclic, or may commence by environmental or other external events.

There are three known primary mechanisms by which an active agent can be released from a delivery system: (a) diffusion, (b) degradation, and (c) swelling followed by diffusion. Any or all of the foregoing mechanisms may occur in one release system.

Diffusion occurs when a drug or other active agent passes through the polymer that forms the controlled release device. The diffusion can occur on a macroscopic scale as through pores in the polymer matrix—or on a molecular level by passing between polymer chains or through microchannels placed in the polymer matrix.

Controlled-release topical delivery systems can be designed so that the system will not release its agent until it is placed in the appropriate biological and environmental conditions. For example, controlled-release systems are initially dry. When placed over the body on the skin, the controlled-release system absorbs water or fluid from the skin (or other body fluids) and will increase in size. The swelling increases the aqueous solvent content within the formulation as well as the polymer mesh size, enabling the therapeutic agent to diffuse through the swollen network into the external environment.

U.S. Pat. No. 2,352,508 discloses a wound dressing comprising a net substrate encapsulated in hydrophilic tacky resin coating leaving the apertures in the net substrate unoccluded. The coating is a polyurethane that may contain active agents such as sulphadiazine, wherein the coated substrate is laminated between two release liners.

U.S. Pat. No. 6,326,410 describes a wound contact layer formed from a polyurethane foam. The foam may deliver active agents.

U.S. Published Application 2002/0128578 describes a medical device comprising multiple sheets having microchannels useful for wound dressing and drug delivery. The articles comprise layers having microchannels that are made of polyurethane or polyvinylacetate to facilitate the delivery of pharmaceutical compounds.

U.S. Pat. No. 6,183,770 describes a patch for delivery of active agents locally to the skin in a manner to minimize the adverse effects of adhesives on active agents.

U.S. Pat. No. 6,352,715 describes a transdermal drug delivery system whereby huperzine, a naturally occurring acetylcholine esterase inhibitor, is administered for the treatment of Alzheimer's Disease. The transdermal delivery device is a patch.

U.S. Pat. No. 7,045,145 describes a transdermal contraceptive delivery system for fertility control in women when synthetic estrogen, ethanol estrodiol and synthetic progestin are dispersed through a patch comprising a backing layer, and an adjoining layer of a solid absorption adhesive.

U.S. Pat. No. 5,919,476 describes a bandage in the form of a reinforced silicone gel sheet for application to scar tissue. The bandage comprises three layers; a tacky skin contacting first layer made from a silicone sheet, a reinforcing second layer comprising a non-liquid permeable mesh fabric support structure having a plurality of holes therethrough and a non-tacky bonding third layer which includes the holes and laminates itself to the first layer, thereby securing the second layer between the first and third layer.

U.S. Pat. No. 5,895,656 describes a gas or gel filled silicone bandage made of silicone sheeting for treating wounds and scar tissue. The flexible silicone sheeting or film contains an interior space that may be filled with dry gas or a hydrophobic gel. Since there is reduced electrical resistance in scar tissue, the use of the hollow space in the bandage may increase the static electrical field or negative charge applied to the scar which could hasten the inhibitatory healing process for hypertrophic and keloid scars. To improve the electric field within the hollow space, small pieces of Teflon™ sheeting or silicone beads may be inserted in the hollow space.

U.S. Pat. No. 5,759,560 describes a silicone thermal plastic sheeting for scar treatment which has two layers, a first layer of a therapeutic agent to be placed on to the skin and a second backing layer of a thermoplastic polymer bonded to the first layer to provide a thick shape to the material.

SUMMARY OF THE INVENTION

The present invention is a controlled-release topical delivery device that is applied to the surface of the skin for delivering one or more therapeutic agents to the skin. The delivery device may have one or multiple layers, with each layer containing one or more therapeutic agents. The delivery device comprises a therapeutic agent, a flexible, encapsulated porous polymer foam material for holding the therapeutic agent within its open cell structure and subsequently releasing the therapeutic agent, and a polymer enrobing material for holding and releasing the encapsulated polymer foam material including the therapeutic agent for delivering the therapeutic agent to the skin. The controlled-release delivery device may have one or more layers comprising one or more therapeutic agents encapsulated within a flexible porous polymer and a polymer enrobing material for holding and releasing the therapeutic agent to the skin for absorption. Any reasonable number of layers or sheets of the polymer may be utilized and integrally formed together for releasing the active therapeutic agent. The particle size of the therapeutic agent and particle size of the flexible polymer with the open cell size become incrementally larger as they are situated in layers contacting the skin and then successively placed outwardly away from the skin. Typically, a smaller particle size of the therapeutically active agent is located in a layer closest to the skin, with the next larger particle size located in a layer adjacent to the layer closest to the skin. A third layer may be placed on the second layer closest to the skin, wherein the third layer comprises therapeutically active agent particles incrementally larger than those in the first and second layers. These particle sizes of therapeutic agent may increase in proportion to their distance from the skin. The size variation assures the proper and continuous dosage of the therapeutic agents distributed to the skin for absorption therein. This arrangement, along with many other factors, allows for the steady, controlled release of therapeutic agents to the skin for extensive periods of time, preferably ranging from a few hours to about four months. The therapeutic agents are typically water soluble and are delivered for systemic use or for treatment of a dermatological conditions or disease. Therapeutic agents that are not water soluble may be conventionally modified for absorption into the skin.

In one aspect, the invention relates to methods of delivery of therapeutic agents to the skin for treating localized and systemic conditions and diseases.

In another aspect, the invention relates to a method of treating wounds.

In yet another aspect, the invention relates to methods of treating or preventing scar tissue.

DETAILED DESCRIPTION OF THE PREFERRED EMBODIMENTS

The present invention may be embodied in other specific forms without departing from the spirit or essential attributes thereof, and it is therefore desired that the present embodiment must be considered in all aspects as illustrative and not restrictive, reference being made to the appended claims rather than to the foregoing description to indicate the scope of the invention.

Figure 1:
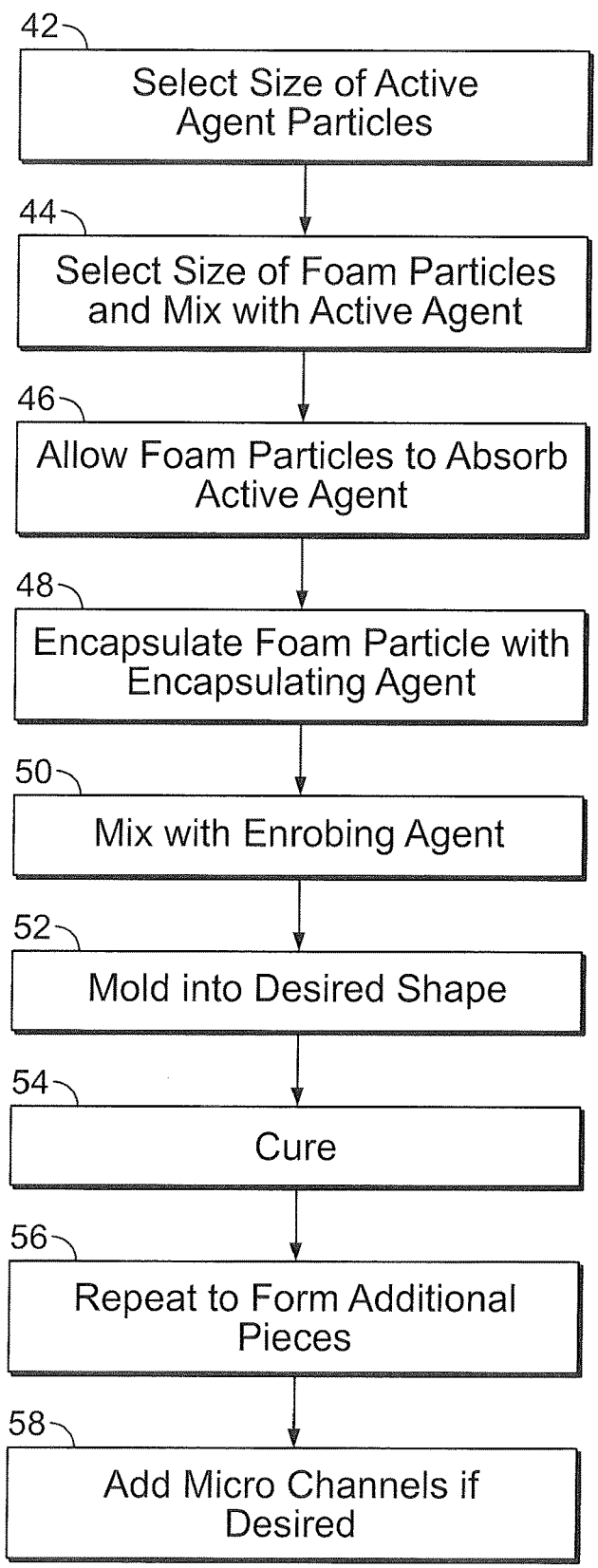
FIG. 1 depicts a flow diagram showing the steps of preparing the multilayer delivery device of the present invention.
Figure 2:
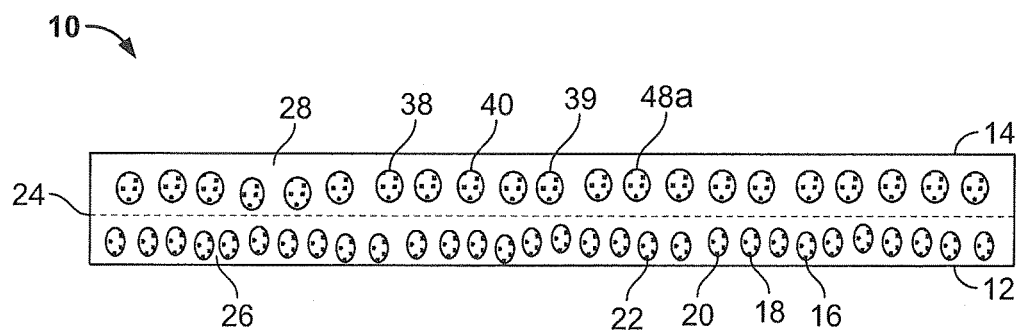
FIG. 2 depicts a first cured layer of enrobing polymer, including encapsulated, therapeutically active agents on which rests a second layer of uncured polymer, including an enrobing polymer having particles of a therapeutically active agent larger than the size of the particles in the first layer.

As seen in FIGS. 2-6, one or more layers of polymer hold one or more therapeutic agents of varying particle size for the controlled release of the agents onto the surface of the skin. One, two, three, or more sizes of therapeutic agent particles can be used in the invention to produce a final product that is a multilayered delivery device, wherein the layers may contain different sizes of foam particles and therapeutic agents. The layers and particle sizes may be designed to meet the specific characteristics of pharmacokinetic profiles of the active agent and the chemical and physical properties of the polymers. Generally, the larger the size of the particle of the therapeutic agent, the longer it takes to be released and distributed to the skin. Therefore, the larger particles are located away from the skin surface. The particle sizes of the therapeutic agent in the layer closest to the skin are typically smaller than the sizes of particles of therapeutic agent positioned away from the skin. The smaller particle size of the therapeutic agent, therefore, is delivered and distributed to the skin surface in a shorter time period than the larger particle sizes. Using this arrangement of specific, successively larger particle sizes and layers of polymers containing the different particle sizes, the controlled rate of release of the therapeutic agents onto the surface of the skin can be adjusted from about substantially immediately to about four months. The practitioner, therefore, can control the rate of release of the therapeutic agent by selecting a specific particle size and type of polymer by using incrementally larger sized particles of therapeutic agent measured from the layer contacting the skin surface to an outward progression from the skin surface. In addition, there are other factors that would contribute to the release rate of the therapeutic agent so that it can be controlled, ranging in hours to months, depending on the following: the particle size of the flexible porous polymer foam material, the particle size of the therapeutic agent, the size of the open cells within the flexible porous polymer foam material, the concentration of the therapeutic agent, the number of particles per unit volume of the enrobing material, the density of the particles per unit volume of the polymer foam and enrobing material, the nature of the physical and chemical properties of the therapeutic agent, the polymer used for encapsulating the open cell foam material and therapeutic agent, and if desired, the use of microchannels that may pass through the layers of polymer, including the size or diameter of the microchannel and the number or amount of microchannels. Controlling the above factors leads to a controlled release rate of the therapeutic agent and the achievement of different release rates of the therapeutic agents.

FIG. 2 shows a cross-section of the delivery device 10 of the present invention comprising a bottom side 12 that contacts the skin surface and a top side 14 indicating the top side of the uppermost layer of polymer. A flexible porous polymer foam material 16 contains particles 18 that may be a polymer foam that is flexible with open foam cells 20. The diameter of the open foam cells generally ranges from about 350 to about 1500 microns to allow for the holding and releasing of therapeutic agents. In the first layer 26, the open cell size may range from about 350 to 650 microns. The foregoing cell size is typical of the diameter of the open cells in the fluid flexible foam material 16. The particle size of the open cells of the polymer foam should be of a size sufficient for holding an amount of a therapeutic agent particles so it can be released or delivered onto the skin through a polymer enrobing material and through a polymer enclosing material for as little as about 4-8 hours to about 120 days, depending upon the number of layers containing varying sizes of particles. The polymer foam material may be selected from hydrophilic or hydrophobic polymers, depending upon the nature of the therapeutic agent and the nature of the enrobing agent. Typical hydrophilic polymer foam materials may be selected from the group consisting of polyurethane, polyvinylacetate, polyvinyl alcohol (PAVE), polyethylene, and medical grade silicone. Preferably, hydrophilic polyurethane is utilized. It is available from the following sources: Runnel, Inc., Boothbay, Me.; and Len dell, Inc., St. Charles, Mo.

Two layers of flexible porous polymer foam material 16 are shown in FIG. 2 with line 24 drawn to separate the first or bottom layer 26, which is cured and contacts the skin surface from the second layer 28. The second layer 28 is applied to the first layer 26 in an uncured state, subject to subsequent curing. Line 24 is shown for illustrative purposes only.

Figure 3:
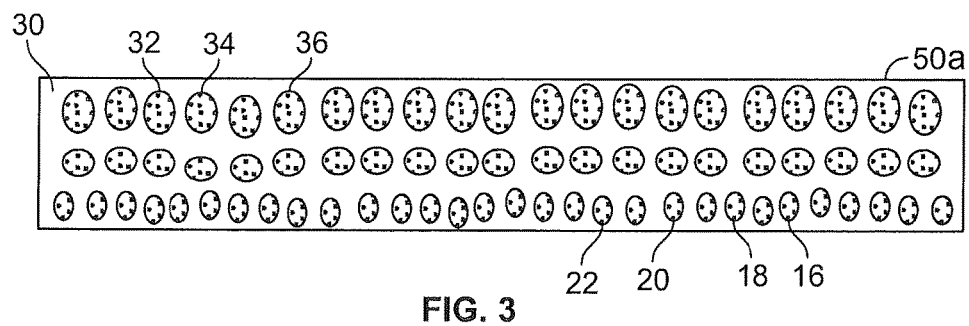
FIG. 3 depicts a cross-section of the controlled-release delivery device of the present invention showing three layers of cured foam particles wherein small-sized particles are closest to the skin, medium-sized particles are located intermediate to the skin, and large-sized particles are located furthest away from the skin.

FIG. 3 shows a third, or in this instance, top layer 30. Foam polymer particles 32 with open foam cells 34 containing absorbed therapeutic agent 36 in third layer 30 are larger in size than the foam polymer particles 38 of open foam cells 40 in second layer 28. Accordingly, foam particles 18, open foam cells 20, and therapeutic agent 22 in first layer 26 are smaller than those in foam polymer particles 38, open foam cells 40, and therapeutic agents 36 in third layer 30 and foam particles 32, open foam cells 38, and therapeutic agent 39 in second layer 28. The smaller the size of the therapeutic agent, the quicker the dissolution and distribution to the skin and absorption into the skin surface. As illustrated in FIG. 3, the top layer 30 may have open foam cells 32 having a diameter of about 950 to about 1500 microns. The second layer 28 may have open foam cells 38 having a diameter of about 650 to about 950 microns. The first layer 26 may have open foam cells 20 having a diameter of about 350 to about 650 microns. The same or different therapeutic agents may be utilized in layers 26, 28, and 30. The particle size of the therapeutic agent should be sufficient to be positioned within the cell size of the respective foam particle. Therefore, the three sizes are interdependent of each other. Typically, the therapeutic agent size, the foam particle size and the open cell size are enlarged successively in polymer layers as they are placed away from the skin surface. The largest sizes of the agent, particles and open cells will be the furthest away from the skin. Accordingly, there is a gradual increase in the sizes of the agent, particles and open cells as they are placed in layers away from the skin surface.

The preparation of the delivery device of the present invention is shown in FIG. 1. The particle size of therapeutic agent is selected in step 42 and the open cell size determined, and then the polymer foam material is selected by the size of the open cell particles. For example, when utilizing larger particles of the therapeutic active agent to be included in a layer away from the skin, larger foam particles are selected, thereby having larger open cell sizes. Foam particles may range in size from 800 to 2500 microns. Preferably, the larger sizes of foam particles, which may be utilized in the second or third layer, have larger particle sizes than the first layer, which has particle sizes ranging from about 800 to about 900 microns. Preferably, particle sizes are 900 to 1400 microns for particles in the second layer and 1400 to 2500 microns for particles in the third layer. These particle sizes should have cell sizes of about 650 to about 1500 microns. However, this is not intended to be limitative, for other sizes of particles, therapeutic agents and open cells may be utilized. The particle sizes of the layer closest to the skin should have a diameter ranging from about 800 to about 900 microns, with the cell size ranging from about 350 to 650 microns. This step is shown as number 44 in FIG. 1. The small foam polymer micro particles may be in the form of a powder, granules, or flakes. They are collected and added to a container wherein measured amounts of the therapeutic active agent are added and mixed with the microparticles. The amount of the therapeutic agent depends on the particle size, foam material, and open cell size. For example, microparticles have a fluid consistency. The therapeutic agent is absorbed into the microparticles as shown in step 46 of FIG. 1. The saturated or soaked foam particles containing the therapeutic agent are then mixed 48 with an encapsulating agent 48*a* so that the entire foam particle including the therapeutic agent within the open cell is surrounded by the encapsulating agent. The encapsulating agent provides another means for sustaining or controlling the release and delivery of the therapeutic agent. Encapsulating agents typically are degradable in the presence of water or fluids released from the skin. Encapsulating agents may be water soluble methacrylates, ethylene vinyl chloride, glycols, alcohols, vinyl acetates, starches, agar, and other gel-like gums and organic urea compounds, for example, polyoxymethylene urea and the like. Preferred encapsulating agents may be selected from the following list. However, it is not intended to be limitative.

poly(2-hydroxy ethyl methacrylate)
poly(N-vinyl pyrrolidone)
poly(methyl methacrylate)
poly(vinyl alcohol)
poly(acrylic acid)
polyacrylamide
poly(ethylene-co-vinyl acetate)
poly(ethylene glycol)
poly(methacrylic acid)

Preferably, encapsulating agents are selected from the group consisting of polylactides (PLA), polyglycolides (PGA), poly(lactide-co-glycolides) (PLGA), m-polyanhydrides, and m-polyorthoesters. The encapsulating agent coating the foam particles affects the delivery time of the therapeutic agent. The encapsulating agents degrade by hydrolysis of their ester linkages in the presence of water or fluids released from the skin.

In step 50, the encapsulated foam particle is enrobed with a polymer enrobing material 50*a*. The polymer enrobing material is preferably a silicone gel or silicone elastomer that is prepared in the form of a sheet. The silicone is soft, durable, and of a medical grade. It may also be a hydrogel or other suitable material, such as ethylene-vinyl acetate or polyurethane elastomers. The encapsulated polymer foam material holding the therapeutic agent is mixed well to ensure uniform and even particle distribution in the enrobing agent mixture. In step 52, the flowable material is placed in a mold having a backing material and then cured at temperatures ranging from about 120° F. to about 300° F. as noted in step 54. Lower temperatures are required to ensure stability of therapeutic agents. With lower temperatures, the curing time is longer. It will take about 10 to about 15 minutes for curing. At higher temperatures, when some therapeutic agents remain stable, the curing time is, for example, about 4-5 minutes. Additional layers can be prepared 56 and added to the top of first layer 26. In FIG. 2, second layer 28 can be added to the top of layer 26 and subsequently cured, which shows the cured layer 26 below uncured layer 28. Upon curing, line or separation 24 is not seen, for the layers are blended together. Additional layers may be added as necessary to provide the intended controlled release of a therapeutic agent for the desired release time. For example, a third layer or top 30 layer can be added and cured with the approximately large-sized foam particles 32, open cell size 34, and therapeutic agent 36. Additional layers can be added accordingly for longer time periods for releasing therapeutic agents.

Conventional hydrogels can be utilized in accordance with the composite sheet of the present invention. Hydrogels are three dimensional hydrophilic polymer networks capable of swelling in water or biological fluids, and retaining a large amount of fluids in the swollen state. Their ability to absorb water is due to the presence of hydrophilic groups such as —OH, —CONH—, —CONH$_2$, —COOH, and —SO$_3$H. The water content in the hydrogels affects different properties like permeability, mechanical properties, surface properties, and biocompatibility. Hydrogels have similar physical properties as that of living tissue, and this similarity is due to the high water content, soft and rubbery consistency, and low interfacial tension with water or biological fluids. The ability of molecules of different size to diffuse into (drug loading), and out (release drug) of hydrogels, permit the use of hydrogels as delivery systems. Since hydrogels have high permeability for water soluble drugs and proteins, the most common mechanism of drug release in the hydrogel system, is diffusion. Factors like polymer composition, water content, crosslinking density, and crystallinity, can be used to control the release rate and release mechanism from hydrogels.

Hydrogels, based on their nature, can be classified as pH sensitive, temperature sensitive, enzyme sensitive, and electrical sensitive. pH sensitive hydrogels can be neutral or ionic in nature. The anionic hydrogels contain negatively charged moieties, cationic networks contain positively charged moieties, and neutral networks contain both positively and negatively charged moieties. In neutral hydrogels, the driving force for swelling arises from the water-polymer thermodynamic mixing contributions, and elastic polymer contributions. In ionic hydrogels, the swelling is due to the previous two contributions, as well as ionic interactions between charged polymer and free ions. The presence of ionizable functional groups like carboxylic acid, sulfonic acid or amine groups, renders the polymer more hydrophilic, and results in high water uptake.

In the case of anionic polymeric network containing carboxylic or sulphonic acid groups, ionization takes place, as the pH of the external swelling medium rises above the pKa of that ionizable moiety.

The best example for hydrogel is: preparation of poly(2-hydroxyethyl methacrylate) hydrogels from hydroxyethyl methacrylate, using ethylene glycol dimethacrylate as crosslinking agent. Using the above method, a great variety of hydrogels have been synthesized. The hydrogels can be made pH-sensitive or temperature-sensitive, by incorporating methacrylic acid, or N-isopropylacrylamide, as monomers.

Polymers containing functional groups like —OH, —COOH, —NH$_2$, are soluble in water. The presence of these functional groups on the polymer chain, can be used to prepare hydrogels by forming covalent linkages between the polymer chains and complementary reactivity, such as amine-carboxylic acid, isocyanate-OH/NH$_2$ or by Schiff base formation.

Gluteraldehyde can be used as a crosslinking agent to prepare hydrogels of polymers containing —OH groups like poly(vinyl alcohol). Also, polymers containing amine groups (albumin, gelatin, polysaccharides), can be cross-linked using gluteraldehyde.

Polymers that are water soluble, can be converted to hydrogels, using big or higher functional crosslinking agents like divinylsulfone, and 1,6-hexanedibromide. The cross-linking agents react with the functional groups present on the polymer, via addition reaction. These crosslinking agents are highly toxic, and hence unreacted agents have to be extracted. Moreover the reaction has to be carried out in organic solvent, as water can react with the crosslinking agent. The drugs have to be loaded after the hydrogels are formed, as a result the release will be typically first order.

Crosslinking between polymers through hydrogen bond formation occurs as in the case of poly(methacrylic acid) and poly(ethylene glycol). The hydrogen bond formation takes place between the oxygen of poly(ethylene glycol) and carboxylic acid group of poly(methacrylic acid). Carriers consisting of networks of poly(methacrylic acid-g-ethylene glycol) showed pH dependent swelling due to the reversible formation of interpolymer complex, stabilized by hydrogen bonding between the etheric groups of the grafted poly (ethylene glycol), and the carboxylic acid protons of the poly(methacrylic acid).

Most of the covalent crosslinking agents are known to be toxic, even in small traces. A method to overcome this problem and to avoid a purification step, is to prepare hydrogels by reversible ionic crosslinking. Chitosan, a polycationic polymer can react with positively charged components, either ions or molecules, forming a network through ionic bridges between the polymeric chains. Among anionic molecules, phosphate bearing groups, particularly sodium tripolyphosphate is widely studied. Ionic crosslinking is a simple and mild procedure. In contrast to covalent cross-linking, no auxiliary molecules such as catalysts are required. Chitosan is also known to form polyelectrolyte complex with poly(acrylic acid). The polyelectrolyte complex undergoes slow erosion, which gives a more biodegradable material than covalently crosslinked hydrogels.

Figure 4:
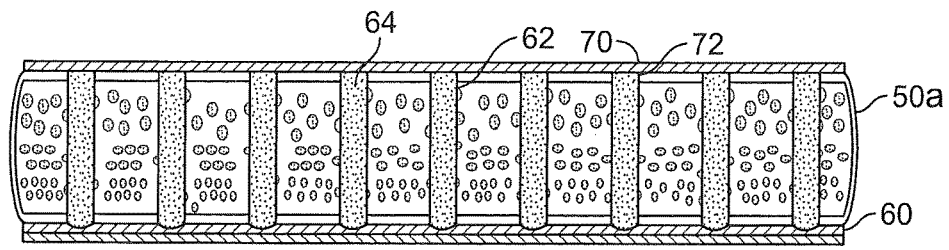
FIG. 4 depicts a cross-section of the controlled-release delivery device wherein there are three cured layers of foam particles, including therein three sizes of therapeutic agents, with microchannels passing vertically there through, the entire cross-section being enclosed in a polymer material.
Figure 5:
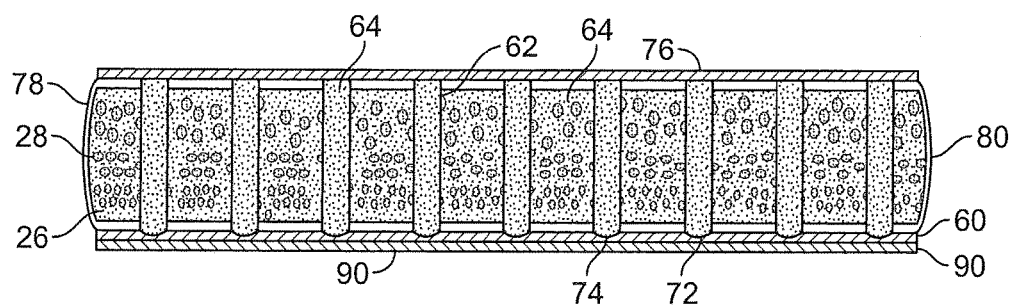
FIG. 5 depicts the encapsulated therapeutic agent dispersed from microchannels into the polymer throughout three layers of the enrobing polymer of the device shown in FIG. 4.

The therapeutic agent will leach out to the external environment upon removal of the backing layer 60 as shown in FIGS. 4 and 5. The layer closest to the skin, the first layer 26 with the smallest particles, will disperse the therapeutic agent first. The second layer 28 disperses the therapeutic agent at a later time and at a slower rate. The controlled release of the active agent in any of the layers is a result of the swelling of the polymer foam particles 16, 32, 38 followed by diffusion. The rate of the release and delivery of the therapeutic agent is dependent upon many factors. Factors that would contribute to the release rate of the therapeutic agent so that it can be controlled, ranging in hours to months, include the particle size of the flexible porous polymer foam material, the particle size of the therapeutic agent, the size of the open cells within the flexible porous polymer foam material, the concentration of the therapeutic agent, the number of particles per unit volume of the enrobing material, the density of the particles per unit volume of the polymer foam and enrobing material, the nature of the physical and chemical properties of the therapeutic agent, the polymer used for encapsulating the open cell foam material and therapeutic agent, and if desired, the use of microchannels that may pass through the layers of polymer.

As indicated at step 58, microchannels can be added to the structure to enhance and control the delivery time of the therapeutic agents. The microchannels can be added by cutting holes or apertures through the sheet material to form a plurality of microchannels throughout the material by any convenient means. The microchannels may have a size or diameter in an amount sufficient to allow the therapeutic agent to pass therethrough. Typically, the microchannels may have diameters ranging from 100 to 10,000 microns. The diameter of the microchannel will affect the release time and the amount of the active therapeutic agent. The larger the size or diameter of the microchannel, the faster the release rate. The apertures may be prepared by mechanical means by inserting rods through the polymer or by laser.

FIG. 4 shows microchannels 62 filled with therapeutic agent 64 that has not yet migrated into the foam polymer material or released to the skin surface. FIG. 5 shows the therapeutic agent 64 dispersed within the enrobing agent 50*a* so that the therapeutic agent is dispersed throughout the composition or composite sheet. The number of microchannels may vary as desired. Typically, the amount of microchannels should be 100 to 10,000 channels per square inch. The higher number of channels relates to a faster release rate so that larger amounts of the therapeutic agent are released in a shorter time.

The timed, controlled release of the active therapeutic agent can be controlled at periods ranging from hours, days and weeks to months. One or more therapeutic agents may be placed in the layered wound dressing. For purposes of description, the one or more therapeutic agents will be known as the at least one therapeutic agent. However, therapeutic agent and the plural therapeutic agents are used throughout the description of the invention with the same meaning. Additionally, the layered wound dressing of composite sheets may be removed after application for cleaning the skin upon which it rests and then replaced on the skin. Typically, layers closer to the skin with smaller particle size correlated to short term degrading material releases the at least one active therapeutic agent first, for example, a few hours, typically for hours, to a two-week period. The subsequent or following layers will start releasing the at least one therapeutic agent upon swelling of the particles and the agent will reach the skin surface generally after the at least one therapeutic agent is released from the first layer and is delivered to the skin surface.

The therapeutic agents that may be utilized with the polymer enrobing material and flexible polymer foam material of the present invention may be any agent suitable for topical application to the skin. For convenience, the term "therapeutic agent" is utilized herein with no intention to be limitative. Hence, this device can be used to treat, modulate, or prevent various cosmetic or noncosmetic conditions, diseases, neoplasms, blemishes, photoaged skin, biologic deficiencies, and nutritional deficiencies. They may be pharmaceutical agents. One aspect of the invention is the delivery of therapeutic agent for treating wounds and for the prevention and treatment of scar tissue. More than one therapeutic agent may be utilized. These agents may be drugs, vitamins, minerals, manufactured substances, interferon, hormones, steroids, natural products, or a combination of these and others. For example, antioxidants and antimicrobials may be loaded into microchannels 62 for release into the flexible foam material 16 and enrobing material 50*a* for release onto the skin surface. Antioxidants are capable of inhibiting oxidation and when used on the surface of the skin, may prevent fibrosis, and can decrease free radical formation when treating wounds and scar tissue. Vitamin E (alpha-tocopherol) is a preferred antioxidant for use in the composite sheet. However, other antioxidants or vitamins may also be utilized, such as Vitamin C, ascorbyl palmitate, butylated hydroxyanisole, butylated hydroxytoluene, and sodium bisulfate or therapeutic oils and plant or animal extracts such as aloe, emu oil, lavender oil, and rose hip oil. The amount of the antioxidant or other agent used is an amount sufficient to partly or completely fill the open foam cells so that the antioxidant is released in a time period ranging from about a few hours to about 50 to about 120 days onto or into the skin. The amount cannot exceed the concentration that will go into and remain in the solution with silicone if silicone is used as the polymer enrobing material. If other materials are used as the polymer enrobing material, they determine the amount of therapeutic agent or additive. The amount of antioxidant that may be used in the present invention, when silicone is used as the enrobing material, may typically range from about 1% to about 10% by weight of the sheet, with about 1.5% to about 5% being preferred. The composite sheet of the present invention allows for the application of medication to the skin or scar tissue for long periods of time without the need for dressing changes.

Antimicrobials may also be loaded or filled into the microchannels of the present invention. Both antimicrobials and antioxidants may reach the skin through the microchannels 62 or through the flexible porous foam material 16 and polymer enrobing agent 50*a*. Both materials may impregnate or be impregnated into the silicone or other enrobing agent for release onto or into the skin. The preferred antimicrobial used as a therapeutic agent for treating wounds is polymixin B sulfate. Other antimicrobials, antivirals, antibiotics, antifungals, and antineoplastic agents may also be used in the present invention if safe for topical application to the skin and are compatible with other ingredients of the composite sheet material. Examples include fusidic acid, bacitracin zinc, perfenadine, gramicidin, silver in various forms and compounds, aminoglycosides, and sulfa-based antibiotics such as silver sulphadine.

The antimicrobials allow the composite sheet to remain on the surface of the skin for extended periods of time because they inhibit bacterial growth and treat infections.

Analgesics can be added to this device for the treatment, control or modulation of painful conditions of the skin or other organs and body systems. Similarly, agents for treating global endocrine and nonendocrine deficiencies can be delivered with this device through the skin for management of a variety of conditions, diseases or deficiencies, for example, platelet derived growth factor.

Steroids, for example, corticosteroids selected from the group consisting of triamcinolone and dexamethasone, may also be delivered to the skin by the present invention When using microchannels, if needed, a thin polymer membrane liner 70 may be utilized to cover apertures 72 on first and second sides 74, 76 and ends 78, 80 of one layer of the composition. The liner can be of any polymeric material that can be removably attached to the sides of the composition or composite sheet material. The polymeric material may be selected from the group consisting of polyethylene, terephathalite, polyethylene terephathalite amorphous, polyethylene terephathalite glycol, polyvinyl chloride, polypropylene, polystyrene, and polyethylene. The preferred polymeric material is polypropylene.

In addition, a rigid polymer strip 90 may be applied to the second side 74 to cover the polymer liner 60 over apertures 72. The strip 90 is removably attached to the second sides 74 or the side to be applied to the skin prior to application of the single-layer or multilayer composite to the skin. The strip 90 is shown in FIGS. 4 and 5.

Figure 6:
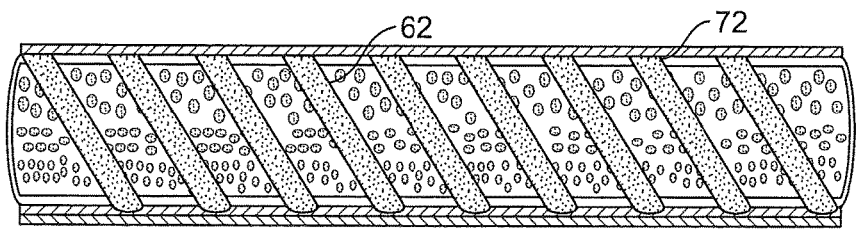
FIG. 6 depicts the device shown in FIG. 4 with microchannels oriented diagonally.

FIG. 6 shows microchannels 62 diagonally positioned in the multilayer device of the present invention. The thickness of the multilayer composite sheet is immaterial. Typically, one sheet of material may range from about 1 to about 1.5 mm in thickness. The composition may be preferably in the form of a rectangular sheet. However, it may be in other sizes and shapes, such as circles, squares, etc., for the shape is not intended to be limiting. In addition, other enrobing materials can be utilized in the invention, and if so, it may be appropriate to use adhesive materials, tapes, bandages, etc. in conjunction with the composite strip to attach the strip to the skin.

For application to the patient, the single-layer or multilayer composition or composite sheet should be applied to the site on the skin to be treated, for example, where it is desired to deliver antibiotics, steroids, etc. or on scar tissue or wounds, etc. The single-layer or multilayer sheet may be secured if the enrobing material is insufficiently tacky or sticky for it adhesion to the skin. The single-layer or multilayer composition or composite sheet does not have to be applied with much pressure or too tightly, for skin irritation may result. However, the use of the material of the present composition usually lessen the chances of skin irritation upon normal and recommended usage. The single-layer or multilayer composition or composite sheet may stay on the skin of the patient for long periods of time, for example, from about 14 to about 30 days, to about 120 days without reapplication. One or more therapeutic agents may typically be used in the device. The single-layer or multilayer composition or composite sheet may be removed for washing the surface of the skin and reapplied, or the skin may be washed around the composition or composite sheet to lessen the chances of infection.

In accordance with the present invention, the release rates or delivery times for the active agent can be controlled to range from substantially immediately upon the placement of the composite sheet on the skin up to 30 days, or up to 60 days or up to 120 days depending upon various factors. These factors include particle size and concentration of the therapeutic agent, as well as the physical and chemical characteristics of the agent, the cell size within the polymer foam material, the particle size of the particle foam material, the number of encapsulated polymer foam particles per unit volume of gel or the density of the microparticles per gel unit volume, the use of microchannels and the size and quantity of microchannels used in the device, and the degradation properties of the encapsulation used to encapsulate the polymer foam particle and therapeutic agent within the open cell of the particle. Manipulation of the foregoing factors results in the controlled release of the therapeutic agent in delivery times desired by the formulator. For example, Table 1 describes representative particle sizes of the therapeutic agent, flexible foam polymer foam material, cell size and various encapsulating agents and enrobing agents, all of which result in the delivery of the therapeutic agent in times ranging from up to a few hours when using one layer to up to sixteen weeks when using multiple layers.

TABLE 1

|  | 1 | 2 | 3 | 4 | 5 | 6 | 7 | 8 |
|---|---|---|---|---|---|---|---|---|
| Agent Particle Size | 200 | 300 | 400 | 500 | 600 | 700 | 800 | 900 |
| Foam Cell Size | 350 | 450 | 550 | 650 | 750 | 850 | 950 | 1050 |
| Foam Particle Size | 800 | 800 | 800 | 800 | 800 | 900 | 1000 | 1100 |
| Encapsulating Agent | PGA | PGA | PGA | PGA | PGA | PGA | PGA | PGA |
| Enrobing Agent | Silicone | silicone | silicone | silicone | silicone | silicone | silicone | silicone |
| Time of Release to Skin Surface | 24 hours | up to 48-72 hours | up to 1 week | greater than 2 weeks | greater than 2 weeks | greater than 2 weeks | 3 weeks | 4 weeks |
|  | 9 | 10 | 11 | 12 | 13 | 14 | 15 | 16 |
| Agent Particle Size | 1000 | 1100 | 1200 | 1200 | 1200 | 1200 | 1200 | 1200 |
| Foam Cell Size | 1150 | 1250 | 1350 | 1450 | 1500 | 1500 | 1500 | 1500 |
| Foam Particle Size | 1200 | 1300 | 1400 | 1500 | 1600 | 2000 | 2200 | 2500 |
| Encapsulating Agent | PGA | PGA | PGA | PGA | PGA | PGA | PGA | PGA |
| Enrobing Agent | silicone | silicone | silicone | silicone | silicone | silicone | silicone | silicone |
| Time of Release to Skin Surface | 5 weeks | 6 weeks | 7 weeks | 8 weeks | 9 weeks | 10 weeks | 14 weeks | 16 weeks |

The foregoing table illustrates typical formulations for producing a single-layered or multilayered composition or composite sheet for applying various therapeutic agents to the skin surface for administration of the agent or treatment of the skin, wound, or scar tissue. Layers of the composite sheet or composition may be combined to yield the desired delivery time of the agent. The number of layers is immaterial for foam particle sizes, cell size, and therapeutic agent particle sizes can be adjusted accordingly by following the progression shown in Table 1. In addition, the therapeutic agent may be placed in microchannels 62 and pass quickly through microchannels for substantially immediate distribution to the skin.

Although the invention has been described with reference to a preferred embodiment, obvious modifications and alterations of the invention may be made without departing from the spirit and scope of the invention. The single-layer or multilayer composition or composite sheet of the present invention may be used for delivering various therapeutic agents to the skin.

The invention claimed is:

1. A multi-layered delivery device, which is applied to the surface of skin for delivering one or more therapeutic agents to the skin, comprising:
    a first layer that contacts the skin, a second layer that contacts the first layer and a third layer that contacts the second layer, each layer comprising;
    particles of one or more therapeutic agents
    particles of flexible, porous, encapsulated polymer open cell foam material, which material is selected from the group consisting of polyurethane, polyvinylacetate, polyvinylalcohol, polyethylene, and silicone for holding and releasing the therapeutic agent;
    a polymer enrobing material selected from the group consisting of silicone, hyrogels ethylene vinyl acetate, and polyurethane elastomers for holding and releasing the encapsulated polymer foam material including the therapeutic agent for delivery to the skin;
    wherein the particle size of the one or more therapeutic agents and the particle size of the flexible polymer with the open cell size become incrementally larger as they are situated in layers contacting the skin and then successively placed outwardly away from the skin, so that a smaller particle size of the therapeutic agent is located in a layer closer to the skin, with the next larger particle size located in a layer adjacent to the layer closest to the skin.

2. The delivery device according to claim 1 wherein the first layer with particles of flexible porous encapsulated polymer foam material having particle sizes ranging from 800 to 900 microns.

3. The delivery device according to claim 1 wherein the second layer with particles of a flexible porous encapsulated polymer foam material having particle sizes ranging from 900 to 1400 microns.

4. The delivery device according to claim 1 wherein the third layer with particles of a flexible porous encapsulated polymer foam material having particle sizes ranging from 1400 to 2500 microns.

5. The delivery device according to claim 1, wherein the particles of the therapeutic agent and the flexible porous polymer are encapsulated by an encapsulating agent.

6. The delivery device according to claim 5, wherein the encapsulating agent is selected from the group consisting of poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), polyethylene glycol), and poly(methacrylic acid).

7. The delivery device according to claim 1, wherein a polymer enrobing material enrobes the encapsulated flexible porous polymer and therapeutic agent.

8. The delivery device according to claim 1, wherein a plurality of microchannels pass through the flexible porous polymer and polymer enrobing material for holding and releasing particles of one or more therapeutic agents.

9. The delivery device according to claim 1, wherein the particle size of the flexible porous materials have a diameter of about 800 to about 2500 microns.

10. The delivery device according to claim 1 wherein the first layer includes open cell sizes ranging from about 350 to 650 microns.

11. The delivery device according to claim 1 wherein the second layer includes open cell sizes ranging from about 650 to 950 microns.

12. The delivery device according to claim 1 wherein the third layer includes open cell sizes ranging from about 950 to 1500 microns.

13. The delivery device according to claim 1, wherein the delivery device has two layers.

14. The delivery device according to claim 1, wherein the delivery device has a plurality of layers for containing therapeutic agents for treating the intended disease, dermatological condition, wound, or scar.

15. The delivery device according to claim 1, wherein the therapeutic agent is selected from the group consisting of polymixin B sulphate, fusidic acid, bacitracin zinc, gramicidin, silver, aminoglysosides, and silver sulphadine.

16. The delivery device according to claim 1, wherein the therapeutic agent is an antioxidant selected from the group consisting of vitamin E, vitamin C, ascorbyl palmitate, butylated hydroxyanisole, butylated hydroxytoluene and sodium bisulfate.

17. The delivery device according to claim 1, wherein the therapeutic agent is a therapeutic oil selected from the group consisting of lavender oil, rose hip oil, aloe vera and emu oil.

18. The delivery device according to claim 1, wherein the therapeutic agent is a hormone.

19. The delivery device according to claim 1, wherein the therapeutic agent is a steroid selected from the group consisting of corticosteroids, triamcinolone and dexamethasone.

20. The delivery device according to claim 1, wherein the therapeutic agent is a pharmaceutical selected from the group consisting of platelet-derived growth factor and pirfnedine.

* * * * *